United States Patent [19]
Speece

[11] Patent Number: 5,626,616
[45] Date of Patent: May 6, 1997

[54] SACROILIAC JOINT MOBILIZATION DEVICE

[76] Inventor: Conrad A. Speece, 10477 Silverock Dr., Dallas, Tex. 75218

[21] Appl. No.: 456,160

[22] Filed: May 31, 1995

[51] Int. Cl.⁶ .................................................. A61F 5/00
[52] U.S. Cl. ...................... 606/240; 128/845; 606/201
[58] Field of Search ............................. 602/19; 128/845; 606/201, 204, 237, 240

[56] References Cited

U.S. PATENT DOCUMENTS

| | | | |
|---|---|---|---|
| 726,055 | 4/1903 | Hartford | 606/240 |
| 1,398,150 | 11/1921 | Pollard | 606/240 |
| 2,818,854 | 1/1958 | Johnson | . |
| 4,579,111 | 4/1986 | Ledesma | 128/845 |
| 4,785,801 | 11/1988 | Speece | . |
| 5,007,414 | 4/1991 | Sexton | 602/19 |
| 5,131,410 | 7/1992 | Neill et al. | 128/845 |
| 5,279,310 | 1/1994 | Hsien | 128/845 |
| 5,390,682 | 2/1995 | Iams | 128/845 |

FOREIGN PATENT DOCUMENTS 2003319  11/1993  Russian Federation ............... 606/237

*Primary Examiner*—Linda C. Dvorak
*Attorney, Agent, or Firm*—Martin Korn

[57] ABSTRACT

A device for localized bone manipulation in the pelvic area of the human body includes a base member. Structure is included within the base member for generating a laterally directed force on each ilium. The structure is disposed substantially parallel to the sacroiliac joints to direct a force generally perpendicular to the sacroiliac joints to thereby spread the pair of ilia apart.

9 Claims, 2 Drawing Sheets

5,626,616

SACROILIAC JOINT MOBILIZATION DEVICE

BACKGROUND OF THE INVENTION

Sacroiliac pain and dysfunction which limits the motion of the pelvis for sitting, standing, and walking results in lower back pain. A large percentage of lower back pain is caused by the sacroiliac joints causing pain down the legs or pain in the lower back. Sacroiliac joints also cause dysfunctions of the pelvis that result in problems in childbirth, bladder and other pelvic disorders, such as, uterine pain and colon pain.

It is important that treatment of the sacroiliac joint be localized to avoid straining adjacent ligaments or joints. The direction and pressure applied must be specific and must be maintained with sufficient force until a release occurs. A need has thus arisen for a device for the treatment of the pelvic area of the body, and particularly the sacroiliac joint which allows for sustained localized treatment, and for the generation of favorable vector forces applied to this joint.

SUMMARY OF THE INVENTION

In accordance with the present invention, a device for localized bone manipulation in the pelvic area including a sacrum, a pair of ilia with a sacroiliac joint disposed between the sacrum and each ilium of the human body is provided. The device includes a base member. Structure is included within the base member for generating a laterally directed force on each ilium. The structure is disposed substantially parallel to the sacroiliac joints to direct a force generally perpendicular to the sacroiliac joints to thereby spread the pair of ilia apart.

BRIEF DESCRIPTION OF THE DRAWINGS

For a more complete understanding of the present invention and for further advantages thereof, reference is now made to the following Description of the Preferred Embodiments taken in conjunction with the accompanying Drawings in which.

DESCRIPTION OF THE PREFERRED EMBODIMENTS

Figure 1:
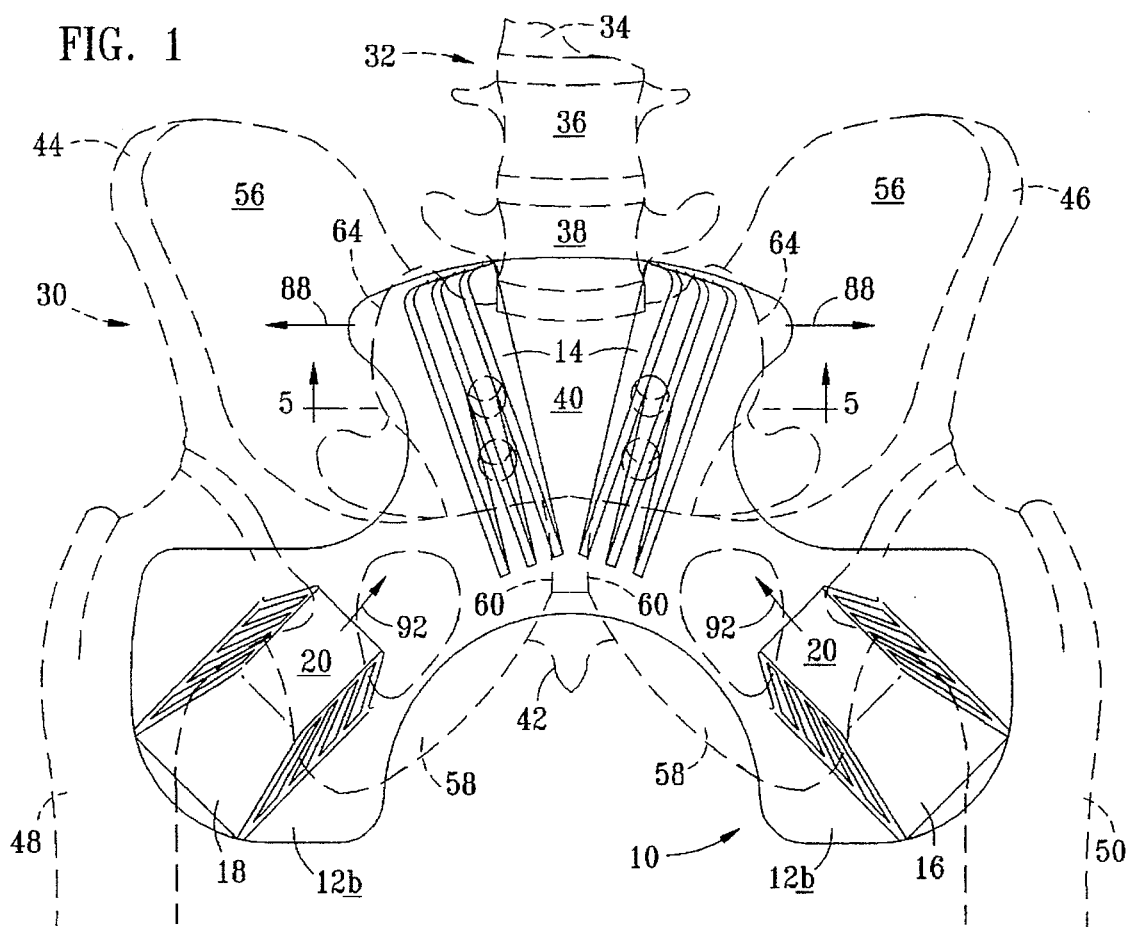
FIG. 1 is a plan view of the present sacroiliac joint mobilization device including a diagrammatic view of the bones of the human pelvis, adjacent spine, and femoral bones shown in dotted lines.
Figure 2:
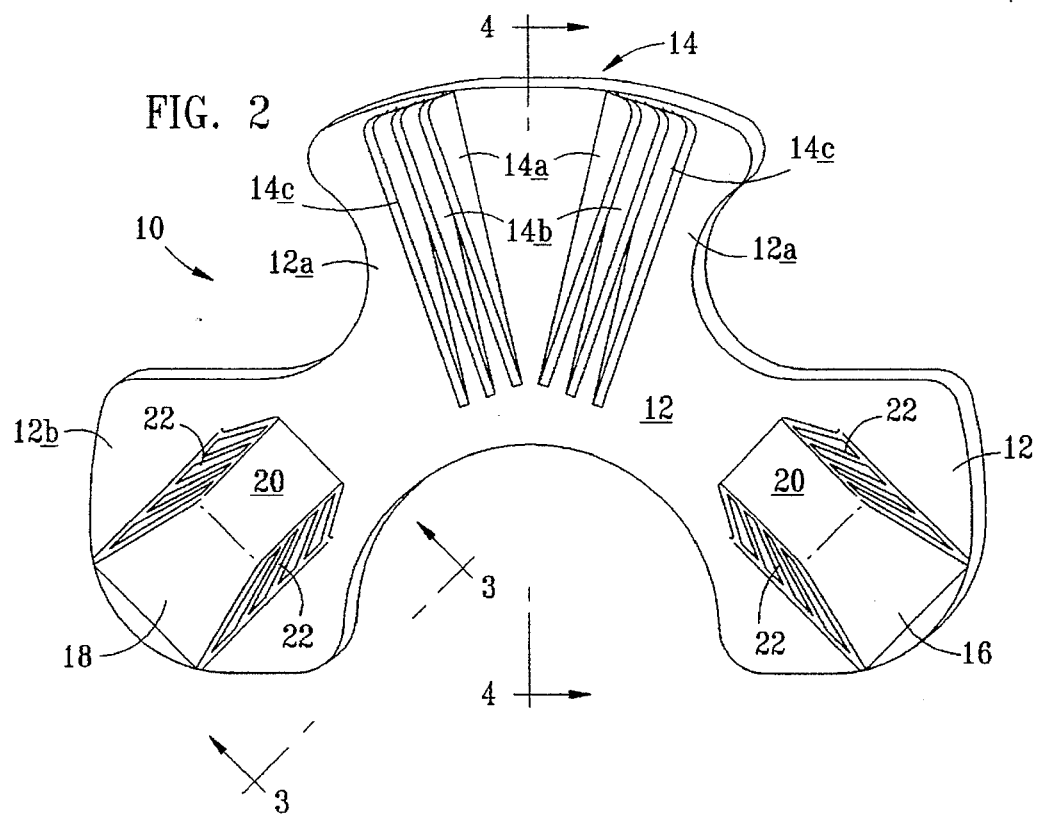
FIG. 2 is a plan view of the present sacroiliac joint mobilization device.
Figure 3:
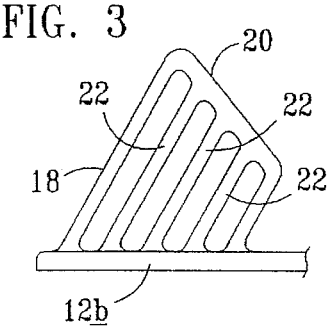
FIG. 3 is a sectional of the present device taken generally along sectional lines 3—3 of FIG. 2.
Figure 4:
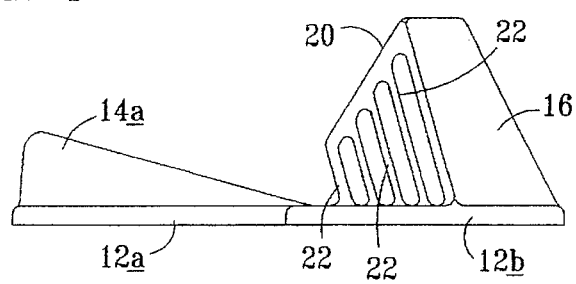
FIG. 4 is a sectional view of the present device taken generally along sectional lines 4—4 of FIG. 2.

Referring simultaneously to FIGS. 1 through 4, the present sacroiliac joint mobilization device is illustrated, and is generally identified by the numeral 10. Sacroiliac joint mobilization device 10 includes a base member 12 having a superior portion 12a and an inferior portion 12b. Superior portion 12a of device 10 includes pairs of spaced apart projections or vanes, generally identified by the numeral 14. Pairs of vanes 14 are indicated by reference numerals 14a, 14b, and 14c. Vanes 14 are angularly disposed with respect to each pair, and are angularly directed outwardly from base member 12.

Disposed on inferior surface 12b of base member 12 is a pair of support members 16 and 18, each having a support surface 20. Support surface 20 is spaced apart from base member 12, and is interconnected to base member 12 utilizing a plurality of spaced apart projections or vanes 22. Support surface 20 is angularly disposed with respect to base member 12 and is superiorly directed.

Vanes 14 and 22 are composed of resilient material which when flexed during use allow vanes 14 to move laterally and vanes 22 to move medially and superiorly. Vanes 14 and 22 may be fabricated from resilient material such as, for example, rubber.

Referring to FIG. 1, the present sacroiliac joint mobilization device 10 is illustrated in a position for localized manipulation of the pelvic area of the human body. Shown in dotted lines in FIG. 1 is an anterior view of the human pelvis. The pelvis is generally identified by the numeral 30. Also shown in FIG. 1 is a portion of the lumbar spine 32 having vertebrae 34, 36, and 38. Located between lumbar spine 32 and the lower limbs are the sacrum 40, coccyx 42, and the laterally and forwardly located innominate bones 44 and 46. Also shown in FIG. 1 are the upper extremities of the left and right femur or thigh bones 48 and 50. Each innominate 44 and 46 includes a portion 56 known as the ilium, a relatively lower portion 58 known as the ischium, and a relatively forwardly located portion 60 known as the pubis. Each ilium 56 includes an auricular surface for articulation with the sacrum 40, and forms a combined pivotal and slidable joint at the area indicated by the reference numeral 64 which is formed between these surfaces known as the sacroiliac joint. The auricular surfaces do not meet directly, there being intervening layers of cartilage and in FIG. 1, the various ligaments are omitted for illustrative purposes only.

Figure 5:
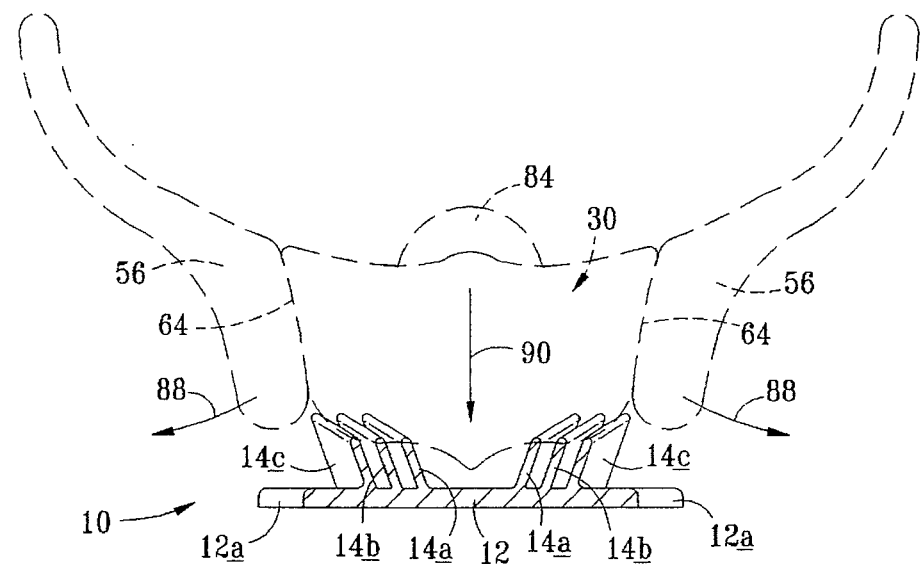
FIG. 5 is a sectional view taken generally along sectional lines 5—5 of FIG. 1 illustrating use of the present sacroiliac joint mobilization device.
Figure 6:
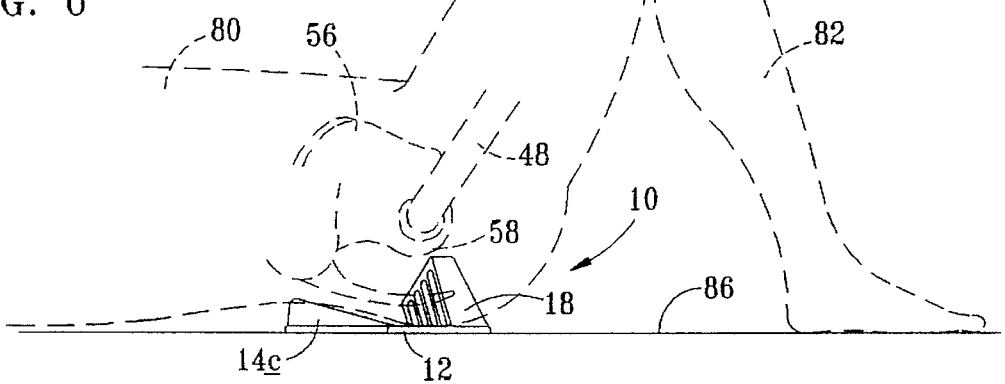
FIG. 6 is a lateral elevation of a patient in the supine, dorsal position utilizing the present sacroiliac joint mobilization device.

Referring simultaneously to FIGS. 1, 5, and 6, the use of the present sacroiliac joint mobilization device 10 is illustrated. Device 10 is positioned under the pelvis 30 of a patient 80 having legs 82, and a head 84. Patient 80 is placed in a supine, dorsal position with the present sacroiliac joint mobilization device 10 in place below the pelvic area 30 of patient 80. Patient 80 is located on the floor or a table 86.

Base member 12 is positioned such that vanes 14 are disposed substantially parallel to sacroiliac joints 64. Vanes 14 generate a laterally directed force on the ilia 56. Further, vanes 14 generate a generally perpendicular force directed to sacroiliac joints 64 to thereby move ilia 56 apart, in the direction of arrows 88. (FIGS. 1 and 5) The gravitational force of patient 80 is directed downwardly against base member 12 as shown by arrow 90 (FIG. 5). Vanes 14 draw sacroiliac joint 64 apart, laterally.

Support members 16 and 18 are generally disposed adjacent to ischium 58. Support surfaces 20 generate superiorly and medially directed forces in the direction of arrows 92 to thereby compress the lower portion of the pelvis 30. The forces generated by vanes 14 in the direction of arrows 88 and the forces generated by support members 16 and 18 in the direction of arrows 92 occur simultaneously to spread sacroiliac joint 64. These forces are localized in the area of sacroiliac joint 64.

While three pairs of vanes 14 are illustrated in the present device 10, a single pair of vanes 14 may be utilized. Multiple pairs of vanes are shown and make it possible to treat different sized pelvises 30. Vanes 14 are spaced apart to lie generally parallel to both sacroiliac joints 64.

It therefore can be seen that the present invention provides for the treatment of strains of the sacroiliac joint through localized mobilization.

Whereas the present invention has been described with respect to specific embodiments thereof, it will be understood that various changes and modifications will be suggested to one skilled in the art and it is intended to encompass such changes and modifications as fall within the scope of the appended claims.

I claim:

1. A device for localized bone manipulation in the pelvic area of the human body, the pelvis having a sacrum, a pair of ilia, and a sacroiliac joint between the sacrum and each ilium, and a pair of ischia, the device comprising:

a base member having a top, bottom, and sides;

first and second force generating means disposed adjacent said base member top and extending upwardly from said base member and outwardly toward said base member sides, said first and second force generating means each being positioned at an angle with respect to said base member and angled with respect to one another for generating laterally directed forces on each ilium said laterally directed forces generated in a direction generally perpendicular to said base member sides when the device is in use, stud first and second force generating means sized and configured to be positioned substantially parallel to the sacroiliac joints to direct a force generally perpendicular to the sacroiliac joints to thereby spread the pair of ilia apart;

third and fourth force generating means disposed adjacent said base member bottom and extending upwardly from said base member and outwardly toward said base member bottom and sized and configured to be positioned adjacent the ischia, said third and fourth force generating means each being positioned at an angle with respect to said base member and angled with respect to one another for generating superiorly and medially directed forces in each ischial area of the pelvis, said superiorly and medially directed forces generated in a direction toward said base member top when the device is in use to thereby compress a lower portion of the pelvis; and said first, second, third, and fourth force generating means positionable to generate forces simultaneously on the pelvis in a direction towards said sides and said top of said base member.

2. The device of claim 1 wherein said first and second force generating means each includes at least one pair of angularly disposed vanes.

3. The device of claim 2 wherein said vanes are flexible.

4. The device of claim 1 wherein said third and fourth force generating means each includes:

support members spaced apart from said base member by a distance and sized and configured to be positioned generally parallel to the ischial areas of the pelvis; and said third and fourth force generating means each extending between said base member and said support members for generating superiorly and medially directed compression forces on a lower portion of the pelvis in a direction toward said top of said base member.

5. The device of claim 4 wherein said third and fourth force generating means each includes a plurality of spaced apart projections interconnecting said base member and said support members.

6. The device of claim 5 wherein said projections are flexible.

7. The device of claim 1 wherein said first and second force generating means each includes at least one pair of angularly disposed vanes;

said third and fourth force generating means each includes support members spaced apart from said base member by a distance and sized and configured to be positioned generally parallel to the ischial areas of the pelvis; and said third and fourth force generating means each extending between said base member and said support members for generating superiorly and medially directed compression forces on a lower portion of the pelvis in a direction toward said top of said base member.

8. The device of claim 7 wherein said third and fourth force generating means each includes a plurality of spaced apart projections interconnecting said base member and said support members.

9. The device of claim 8 wherein said first and second force generating vanes are flexible; and said third and fourth force generating means projections are flexible.

* * * * *